(12) United States Patent
Ishii et al.

(10) Patent No.: US 6,387,683 B1
(45) Date of Patent: May 14, 2002

(54) RECOMBINANT YEAST PDI AND PROCESS FOR PRODUCTION THEREOF

(75) Inventors: Nobuyoshi Ishii, Tokyo; Yasuo Suzuki, Chiba-ken; Kohji Uchida, Shiga-ken; Yushi Matuo, Osaka; Hideo Tanaka, Ibaraki-ken, all of (JP)

(73) Assignee: Oriental Yeast Co., Ltd., Tokyo (JP)

( * ) Notice: Subject to any disclaimer, the term of this patent is extended or adjusted under 35 U.S.C. 154(b) by 0 days.

(21) Appl. No.: 09/368,588

(22) Filed: Aug. 5, 1999

Related U.S. Application Data

(63) Continuation of application No. PCT/JP98/00498, filed on Feb. 6, 1998.

(30) Foreign Application Priority Data

Feb. 7, 1997 (JP) ............................................. 9-038588

(51) Int. Cl.$^7$ ............................. C12N 9/90; C12N 1/20; C12N 15/00; C12P 21/06; C07H 21/04
(52) U.S. Cl. ................... 435/233; 435/69.1; 435/252.3; 435/320.1; 435/942; 536/232; 530/350
(58) Field of Search ................................ 435/233, 69.1, 435/252.3, 320.1, 942; 536/23.2; 530/350

(56) References Cited

FOREIGN PATENT DOCUMENTS

| JP | 197176 | 7/1992 |
| JP | 30967 | 2/1993 |
| JP | 289267 | 11/1995 |

OTHER PUBLICATIONS

Denecke et al., Plant and mammalian sorting signals for protein retention in the endoplasmic reticulum contain a conserved epitope, The EMBO Journal, vol. 11, No. 6, pp. 2345–2355, 1992.
J. Biochem., 108, p. 846–851 (1990).
Cell 74, 899, 1993, M. Lamantia et al.
J. Biochem., 110, p. 306–313 (1991).
Agric. Biol. Chem. 54(4), p. 1043–1044, 1990.

*Primary Examiner*—Tekchand Saidha
(74) *Attorney, Agent, or Firm*—Nixon & Vanderhye P.C.

(57) ABSTRACT

The present invention provides a process for producing biologically active recombinant yeast protein disulfide isomerase, which includes the steps of: a) deleting, substituting, or adding one or more bases in a region encoding an endoplasmic reticulum retention signal in a gene encoding protein disulfide isomerase of yeast to modify the gene so as not to encode part or all of the endoplasmic reticulum retention signal; b) incorporating the modified gene into an expression vector; c) transforming host cells with the expression vector; and d) culturing the host cells transformed with the expression vector in a culture medium kept at a nearly neutral pH, thereby causing protein disulfide isomerase to be secreted in an active state outside the host cells. According to the process of the invention, recombinant yeast protein disulfide isomerase can be secreted in a large amount in a biologically active state into a culture medium, and can be collected by a simple purification method.

5 Claims, 11 Drawing Sheets

Progress of culture of Saccharomyces cerevisiae P1, Y3
100 mL broth, 500 mL Sakaguchi flask 30°C, 105 rpm
● : P1 Strain, UOD    ○ : Y3 Strain, UOD
▲ : P1 Strain, pH    △ : Y3 Strain, pH

Fig. 2

| | | | | | | | | | | | | | | | |
|---|---|---|---|---|---|---|---|---|---|---|---|---|---|---|---|
| ATG | AAG | TTT | TCT | GCT | GGT | GCC | GTC | CTG | TCA | TGG | TCC | TCC | CTG | CTG | 45 |
| Met | Lys | Phe | Ser | Ala | Gly | Ala | Val | Leu | Ser | Trp | Ser | Ser | Leu | Leu | |
| | | | | 5 | | | | | 10 | | | | | 15 | |
| CTC | GCC | TCC | TCT | GTT | TTC | GCC | CAA | CAA | GAG | GCT | GTG | GCC | CCT | GAA | 90 |
| Leu | Ala | Ser | Ser | Val | Phe | Ala | Gln | Gln | Glu | Ala | Val | Ala | Pro | Glu | |
| | | | | 20 | | | | | 25 | | | | | 30 | |
| GAC | TCC | CTG | TCG | TTA | AGT | TGG | CCA | CCG | ACT | CTT | TCA | ATG | AAT | ACA | 135 |
| Asp | Ser | Leu | Ser | Leu | Ser | Trp | Pro | Pro | Thr | Leu | Ser | Met | Asn | Thr | |
| | | | | 35 | | | | | 40 | | | | | 45 | |
| TTC | AGT | CGC | ACG | ACT | TGG | TGG | CTT | GCG | GAG | TTT | TTT | GCT | CCA | TGG | 180 |
| Phe | Ser | Arg | Thr | Thr | Trp | Trp | Leu | Ala | Glu | Phe | Phe | Ala | Pro | Trp | |
| | | | | 50 | | | | | 55 | | | | | 60 | |
| TGT | GGC | CAC | TGT | AAG | AAC | ATG | GCT | CCT | GAA | TAC | GTT | AAA | GCC | GCC | 225 |
| Cys | Gly | His | Cys | Lys | Asn | Met | Ala | Pro | Glu | Tyr | Val | Lys | Ala | Ala | |
| | | | | 65 | | | | | 70 | | | | | 75 | |
| GAG | ACT | TTA | GTT | GAG | AAA | AAC | ATT | ACC | TTG | GCC | CAG | ATC | GAC | TGT | 270 |
| Glu | Thr | Leu | Val | Glu | Lys | Asn | Ile | Thr | Leu | Ala | Gln | Ile | Asp | Cys | |
| | | | | 80 | | | | | 85 | | | | | 90 | |
| ACT | GAA | AAC | CAG | GAT | CTG | TGT | ATG | GAA | CAC | AAC | ATT | CCA | GGG | TTC | 315 |
| Thr | Glu | Asn | Gln | Asp | Leu | Cys | Met | Glu | His | Asn | Ile | Pro | Gly | Phe | |
| | | | | 95 | | | | | 100 | | | | | 105 | |
| CCA | AGC | TTG | AAG | ATT | TTC | AAA | AAC | AGC | GAT | GTT | AAC | AAC | TCG | ATC | 360 |
| Pro | Ser | Leu | Lys | Ile | Phe | Lys | Asn | Ser | Asp | Val | Asn | Asn | Ser | Ile | |
| | | | | 110 | | | | | 115 | | | | | 120 | |
| GAT | TAC | GAG | GGA | CCT | AGA | ACT | GCC | GAG | GCC | ATT | GTC | CAA | TTC | ATG | 405 |
| Asp | Tyr | Glu | Gly | Pro | Arg | Thr | Ala | Glu | Ala | Ile | Val | Gln | Phe | Met | |
| | | | | 125 | | | | | 130 | | | | | 135 | |
| ATC | AAG | CAA | AGC | CAA | CCG | GCT | GTC | GCC | GTT | GTT | GCT | GAT | CTA | CCA | 450 |
| Ile | Lys | Gln | Ser | Gln | Pro | Ala | Val | Ala | Val | Val | Ala | Asp | Leu | Pro | |
| | | | | 140 | | | | | 145 | | | | | 150 | |
| GCT | TAC | CTT | GCT | AAC | GAG | ACT | TTT | GTC | ACT | CCA | GTT | ATC | GTC | CAA | 495 |
| Ala | Tyr | Leu | Ala | Asn | Glu | Thr | Phe | Val | Thr | Pro | Val | Ile | Val | Gln | |
| | | | | 155 | | | | | 160 | | | | | 165 | |
| TCC | GGT | AAG | ATT | GAC | GCC | GAC | TTC | AAC | GCC | ACC | TTT | TAC | TCC | ATG | 540 |
| Ser | Gly | Lys | Ile | Asp | Ala | Asp | Phe | Asn | Ala | Thr | Phe | Tyr | Ser | Met | |
| | | | | 170 | | | | | 175 | | | | | 180 | |
| GCC | AAC | AAA | CAC | TTC | AAC | GAC | TAC | GAC | TTT | GTC | TCC | GCT | GAA | AAC | 585 |
| Ala | Asn | Lys | His | Phe | Asn | Asp | Tyr | Asp | Phe | Val | Ser | Ala | Glu | Asn | |
| | | | | 185 | | | | | 190 | | | | | 195 | |

Fig. 3

| | |
|---|---|
| GCA GAG GAT GAT TTC AAG CTT TCT ATT TAC TTG CCC TCC GCC ATG<br>Ala Glu Asp Asp Phe Lys Leu Ser Ile Tyr Leu Pro Ser Ala Met<br>200                    205               210 | 630 |
| GAC GAG CCT GTA GTA TAC AAC GGT AAG AAA GCC GAT ATC GCT GAC<br>Asp Glu Pro Val Val Tyr Asn Gly Lys Lys Ala Asp Ile Ala Asp<br>215               220              225 | 675 |
| GCT GAT GTT TTT GAA AAA TGG TTG CAA GTG GAA GCC TTG CCC TAC<br>Ala Asp Val Phe Glu Lys Trp Leu Gln Val Glu Ala Leu Pro Tyr<br>230             235              240 | 720 |
| TTT GGT GAA ATC GAC GGT TCC GTT TTC GCC CAA TAC GTC GAA AGC<br>Phe Gly Glu Ile Asp Gly Ser Val Phe Ala Gln Tyr Val Glu Ser<br>245             250              255 | 765 |
| GGT TTG CCT TTG GGT TAC TTG TTC TAC AAT GAC GAG GAA GAA TTG<br>Gly Leu Pro Leu Gly Tyr Leu Phe Tyr Asn Asp Glu Glu Glu Leu<br>260             265              270 | 810 |
| GAA GAA TAC AAG CCT CTC TTT ACC GAG TTG GCC AAA AAG AAC AGA<br>Glu Glu Tyr Lys Pro Leu Phe Thr Glu Leu Ala Lys Lys Asn Arg<br>275             280              285 | 855 |
| GGT CTA ATG AAC TTT GTT AGC ATC GAT GCC AGA AAA TTC GGC AGA<br>Gly Leu Met Asn Phe Val Ser Ile Asp Ala Arg Lys Phe Gly Arg<br>290             305              300 | 900 |
| CAC GCC GGC AAC TTG AAC ATG AAG GAA CAA TTC CCT CTA TTT GCC<br>His Ala Gly Asn Leu Asn Met Lys Glu Gln Phe Pro Leu Phe Ala<br>305             310              315 | 945 |
| ATC CAC GAC ATG ACT GAA GAC TTG AAG TAC GGT TTG CCT CAA CTC<br>Ile His Asp Met Thr Glu Asp Leu Lys Tyr Gly Leu Pro Gln Leu<br>320             325              330 | 990 |
| TCT GAA GAG GCG TTT GAC GAA TTG AGC GAC AAG ATC GTG TTG GAG<br>Ser Glu Glu Ala Phe Asp Glu Leu Ser Asp Lys Ile Val Leu Glu<br>335             340              345 | 1035 |
| TCC AAG GCT ATT GAA CCT TTG GTT AAG GAC TTC TTG AAA GGT GAT<br>Ser Lys Ala Ile Glu Pro Leu Val Lys Asp Phe Leu Lys Gly Asp<br>350             355              360 | 1080 |
| GCC TCC CCA ATC GTG AAG TCC CAA GAG ATC TTC GAG AAC CAA GAT<br>Ala Ser Pro Ile Val Lys Ser Gln Glu Ile Phe Glu Asn Gln Asp<br>365             370              375 | 1125 |
| TCC TCT GTC TTC CAA TTG GTC GGT AAG AAC CAT GAC GAA ATC GTC<br>Ser Ser Val Phe Gln Leu Val Gly Lys Asn His Asp Glu Ile Val<br>380             385              390 | 1170 |

Fig. 4

```
AAC GAC CCA AAG AAG GAC GTT CTT GTT TTG TAC TAT GCC CCA TGG    1215
Asn Asp Pro Lys Lys Asp Val Leu Val Leu Tyr Tyr Ala Pro Trp
            395             400             405

TGT GGT CAC TGT AAG AGA TTG GCC CCA ACT TAC CAA GAA CTA GCT    1260
Cys Gly His Cys Lys Arg Leu Ala Pro Thr Tyr Gln Glu Leu Ala
            410             415             420

GAT ACC TAC GCC AAC GCC ACA TCC GAC GTT TTG ATT GCT AAA CTA    1305
Asp Thr Tyr Ala Asn Ala Thr Ser Asp Val Leu Ile Ala Lys Leu
            425             430             435

GAC CAC ACT GAA AAC GAT GTC AGA GGC GTC GTA ATT GAA GGT TAC    1350
Asp His Thr Glu Asn Asp Val Arg Gly Val Val Ile Glu Gly Tyr
            440             445             450

CCA ACA ATC GTC TTC TAC CCA GGT GGT AAG AAG TCC GAA TCT GTT    1395
Pro Thr Ile Val Phe Tyr Pro Gly Gly Lys Lys Ser Glu Ser Val
            455             460             465

GTG TAC CAA GGT TCA AGA TCC TTG GAC TCT TTA TTC GAC TTC ATC    1440
Val Tyr Gln Gly Ser Arg Ser Leu Asp Ser Leu Phe Asp Phe Ile
            470             475             480

AAG GAA AAC GGT CAC TTC GAC GTC GAC GGT AAG GCC TTG TAC GAA    1485
Lys Glu Asn Gly His Phe Asp Val Asp Gly Lys Ala Leu Tyr Glu
            485             490             495

GAA GCC CAG GAA AAG GCT GCT GAG GAA GCC GAT GCT GAC GCT GAA    1530
Glu Ala Gln Glu Lys Ala Ala Glu Glu Ala Asp Ala Asp Ala Glu
            500             505             510

TTG GCT GAC GAA GAA GAT GCC ATT CAC GAT GAA TTG TAA            1569
Leu Ala Asp Glu Glu Asp Ala Ile His Asp Glu Leu ***
            515             520 522
```

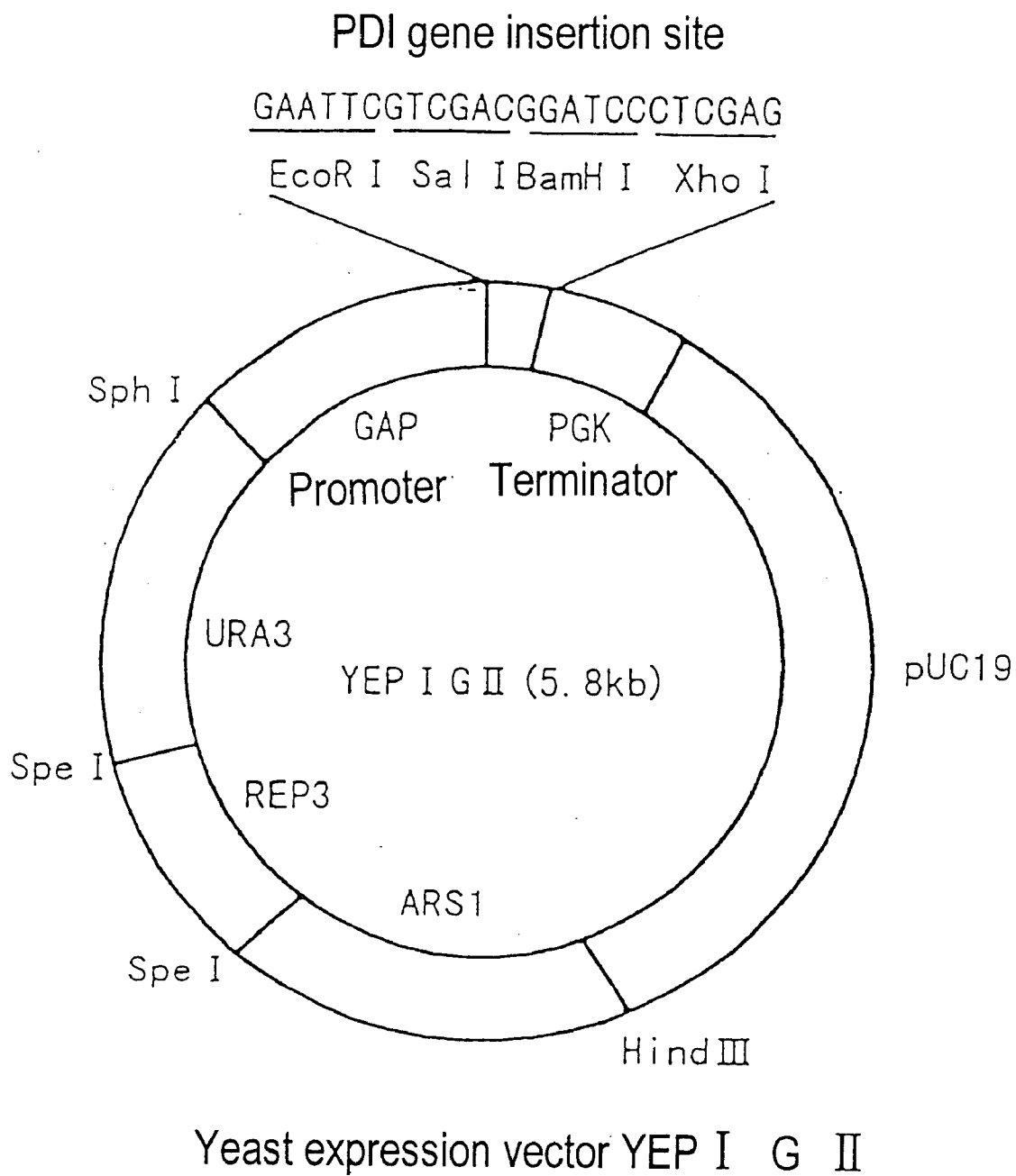

Fig. 6

```
                                                                        BglII cleavage site
     1  AGATCT GGGC  CTCGTGATAC  GCCTATTTTT  ATAGGTTAAT  GTCATGATAA  TAATGGTTTC
    61  TTAGACGTCA  GGTGGCACTT  TTCGGGGAAA  TGTGCGCGGA  ACCCCTATTT  GTTTATTTTT
   121  CTAAATACAT  TCAAATATGT  ATCCGCTCAT  GAGACAATAA  CCCTGATAAA  TGCTTCAATA
   181  ATATTGAAAA  AGGAAGAGTA  TGAGTATTCA  ACATTTCCGT  GTCGCCCTTA  TTCCCTTTTT
   241  TGCGGCATTT  TGCCTTCCTG  TTTTTGCTCA  CCCAGAAACG  CTGGTGAAAG  TAAAAGATGC
   301  TGAAGATCAG  TTGGGTGCAC  GAGTGGGTTA  CATCGAACTG  GATCTCAACA  GCGGTAAGAT
   361  CCTTGAGAGT  TTTCGCCCCG  AAGAACGTTT  TCCAATGATG  AGCACTTTTA  AAGTTCTGCT
   421  ATGTGGCGCG  GTATTATCCC  GTATTGACGC  CGGGCAAGAG  CAACTCGGTC  GCCGCATACA
   481  CTATTCTCAG  AATGACTTGG  TTGAGTACTC  ACCAGTCACA  GAAAAGCATC  TTACGGATGG
   541  CATGACAGTA  AGAGAATTAT  GCAGTGCTGC  CATAACCATG  AGTGATAACA  CTGCGGCCAA
   601  CTTACTTCTG  ACAACGATCG  GAGGACCGAA  GGAGCTAACC  GCTTTTTTGC  ACAACATGGG
   661  GGATCATGTA  ACTCGCCTTG  ATCGTTGGGA  ACCGGAGCTG  AATGAAGCCA  TACCAAACGA
   721  CGAGCGTGAC  ACCACGATGC  CTGTAGCAAT  GGCAACAACG  TTGCGCAAAC  TATTAACTGG
   781  CGAACTACTT  ACTCTAGCTT  CCCGGCAACA  ATTAATAGAC  TGGATGGAGG  CGGATAAAGT
   841  TGCAGGACCA  CTTCTGCGCT  CGGCCCTTCC  GGCTGGCTGG  TTTATTGCTG  ATAAATCTGG
   901  AGCCGGTGAG  CGTGGGTCTC  GCGGTATCAT  TGCAGCACTG  GGGCCAGATG  GTAAGCCCTC
   961  CCGTATCGTA  GTTATCTACA  CGACGGGGAG  TCAGGCAACT  ATGGATGAAC  GAAATAGACA
  1021  GATCGCTGAG  ATAGGTGCCT  CACTGATTAA  GCATTGGTAA  CTGTCAGACC  AAGTTTACTC
  1081  ATATATACTT  TAGATTGATT  TAAAACTTCA  TTTTTAATTT  AAAAGGATCT  AGGTGAAGAT
  1141  CCTTTTTGAT  AATCTCATGA  CCAAAATCCC  TTAACGTGAG  TTTTCGTTCC  ACTGAGCGTC
  1201  AGACCCCGTA  GAAAAGATCA  AAGGATCTTC  TTGAGATCCT  TTTTTTCTGC  GCGTAATCTG
  1261  CTGCTTGCAA  ACAAAAAAAC  CACCGCTACC  AGCGGTGGTT  TGTTTGCCGG  ATCAAGAGCT
```

Sequence of pUC19

Fig. 7

```
      Sequence of pUC19                                              HindIII cleavage site    Sequence of ARS1
      ──────────────────────────────────────────────────────────────▶            ◀──────────────

1321  ACCAACTCTT TTTCCGAAGG TAACTGGCTT CAGCAGAGCG CAGATACCAA ATACTGTCCT
1381  TCTAGTGTAG CCGTAGTTAG GCCACCACTT CAAGAACTCT GTAGCACCGC CTACATACCT
1420  CGCTCTGCTA ATCCTGTTAC CAGTGGCTGC TGCCAGTGGC GATAAGTCGT GTCTTACCGG
1501  GTTGGACTCA AGACGATAGT TACCGGATAA GGCGCAGCGG TCGGGCTGAA CGGGGGGTTC
1561  GTGCACACAG CCCAGCTTGG AGCGAACGAC CTACACCGAA CTGAGATACC TACAGCGTGA
1621  GCTATGAGAA AGCGCCACGC TTCCCGAAGG GAGAAAGGCG GACAGGTATC CGGTAAGCGG
1681  CAGGGTCGGA ACAGGAGAGC GCACGAGGGA GCTTCCAGGG GGAAACGCCT GGTATCTTTA
1741  TAGTCCTGTC GGGTTTCGCC ACCTCTGACT TGAGCGTCGA TTTTTGTGAT GCTCGTCAGG
1801  GGGGCGGAGC CTATGGAAAA ACGCCAGCAA CGCGGCCTTT TTACGGTTCC TGGCCTTTTG
1861  CTGGCCTTTT GCTCACATGT TCTTTCCTGC GTTATCCCCT GATTCTGTGG ATAACCGTAT
1921  TACCGCCTTT GAGTGAGCTG ATACCGCTCG CCGCAGCCGA ACGACCGAGC GCAGCGAGTC
1981  AGTGAGCGAG GAAGCGGAAG AGCGCCCAAT ACGCAAACCG CCTCTCCCCG CGCGTTGGCC
2041  GATTCATTAA TGCAGCTGGC ACGACAGGTT TCCCGACTGG AAAGCGGGCA GTGAGCGCAA
2101  CGCAATTAAT GTGAGTTAGC TCACTCATTA GGCACCCCAG GCTTTACACT TTATGCTTCC
2161  GGCTCGTATG TTGTGTGGAA TTGTGAGCGG ATAACAATTT CACACAGGAA ACAGCTATGA
2221  CCATGATTAC GCC AAGCTT A CATTTTATGT TAGCTGGTGG ACTGACGCCA GAAAATGTTG
2281  GTGATGCGCT TAGATTAAAT GGCGTTATTG GTGTTGATGT AAGCGGAGGT GTGGAGACAA
2341  ATGGTGTAAA AGACTCTAAC AAAATAGCAA ATTTCGTCAA AAATGCTAAG AAATAGGTTA
2401  TTACTGAGTA GTATTTATTT AAGTATTGTT TGTGCACTTG CCTGCAGGCC TTTTGAAAAG
2461  CAAGCATAAA AGATCTAAAC ATAAAATCTG TAAAATAACA AGATGTAAAG ATAATGCTAA
2521  ATCATTTGGC TTTTTGATTG ATTGTACAGG AAAATATACA TCGCAGGGGG TTGACTTTTA
2581  CCATTTCACC GCAATGGAAT CAAACTTGTT GAAGAGAATG TTCACAGGCG CATACGCTAC
2641  AATGACCCGA TTCTTGCTAG CCTTTTCTCG GTCTTGCAAA CAACCGCCGG CAGCTTAGTA
```

Fig. 8

```
2701  TATAAATACA CATGTACATA CCTCTCTCCG TATCCCTCGTA ATCATTTTCT TGTATTTATC
2761  GTCTTTTCGC TGTAAAAACT TTATCACACT TATCTCAAAT ACACTTATTA ACCGCTTTTA
2820  CTATTATCTT CTACGCTGAC AGTAATATCA AACAGTGACA CATATTAAAC ACAGTGGTTT
2881  CTTTGCATAA ACACCATCAG CCTCAAGTCG ATTTCGTGTT CATGCAGATA
2941  GATAACAATC TATATGTTGA TAATTAGCGT TGCCCTCATCA ATGCGAGATC CGTTTAACCG
3001  GACCCTAGTG CACTTACCCC ACGTTCGGTC CACTGTGTGC CGAACATGCT CCTTCACTAT
3061  TTTAACATGT GG[ACTAGT]CT CGGGATGCAT TTTTGTAGAA CAAAAAAGAA GTATAGATTC         spe I cleavage site
3121  TTTGTTGGTA AAATAGCGCT CTCGCGTTGC ATTTCTGTTC TGTAAAAATG CAGCTCAGAT         Sequence of
3181  TCTTTGTTTG AAAAATTAGC GCTCTCGCGT TGCATTTTTG TTTTACAAAA ATGAAGCACA         REP3
3241  GATTCTTCGT TGGTAAAATA GCGCTTTCGC GTTGCATTTC TGTTCTGTAA AAATGCAGCT
3301  CAGATTCTTT GTTTGAAAAA TTAGCGCTCT CGCGTTGCAT TTTTGTTCTA CAAAATGAAG
3361  CACAGATGCT TCGTTAACAA AGATATGCTA TTGAAGTGCA AGATGGAAAC GCAGAAAATG
3421  AACCGGGGAT GCGACGTGCA AGATTACCTA TGCAATAGAT GCAATAGTTT CTCCAGGAAC
3481  CGAAATACAT ACATTGTCTT CCGTAAAGCG CTAGACTATA TATTATTATA CAGGTTCAAA
3541  TATACTATCT GTTTCAGGGA AAACTCCCAG GTTCGGATGT TCAAAATTCA ATGATGGGTA
3601  ACAAGTACGA TCGTAAATCT GTAAAACAGT TTGTCGGATA TTAGGCTGTA TCTCCTCAAA
3661  GCGTATTCGA ATATCATTGA GAAGCTGCAG [ACTAGT]TTT CAATTCAATT CATCATTTTT    spe I cleavage site
3721  TTTTTATTCT TTTTTTTGAT TTCGGTTTCT TTGAAATTTT TTTGATTCGG TAATCTCCGA         Sequence of
3781  ACAGAAGGAA GAACGAAGGA AGGAGCACAG ACTTAGATTG GTATATATAC GCATATGTAG         URA3
3841  TGTTGAAGAA ACATGAAATT GCCCAGTATT CTTAACCCAA CTGCACAGAA CAAAAACCTG
3901  CAGGAAACGA AGATAAATCA TGTCGAAAGC TACATATAAG GAACGTGCTG CTACTCATCC
3961  TAGTCCTGTT GCTGCCAAGC TATTTAATAT CATGCACGAA AAGCAAACAA ACTTGTGTGC
4021  TTCATTGGAT GTTCGTACCA CCAAGGAATT ACTGGAGTTA GTTGAAGCAT TAGGTCCCAA
```

Fig. 9

```
4081  AATTTGTTTA CTAAAAACAC ATGTGGATAT CTTGACTGAT TTTTCCATGG AGGGCACAGT
4141  TAAGCCCGCTA AAGGCATTAT CCGCCAAGTA CAATTTTTTA CTCTTCGAAG ACAGAAAATT
4201  TGCTGACATT GGTAATACAG TCAAATTGCA GTACTCTGCG GGTGTATACA GAATAGCAGA
4261  ATGGGCAGAC ATTACGAATG CACACGGTGT GGTGGGCCCA GGTATTGTTA GCGGTTTGAA
4321  GCAGGCGGCA GAAGAAGTAA CAAAGGAACC TAGAGGCCTT TTGATGTTAG CAGAATTGTC
4381  ATGCAAGGGC TCCCTATCTA CTGGAGAATA TACTAAGGGT ACTGTTGACA TTGCGAAGAG
4441  CGACAAAGAT TTTGTTATCG GCTTTATTGC TCAAAGAGAC ATGGGTGGAA GAGATGAAGG
4501  TTACGATTGG CACCCGGTGT GGGTTTAGAT GACAAGGGAG ACGCATTGGG
4561  TCAACAGTAT AGAACCGTGG ATGATGTGGT CTCTACAGGA TCTGACATTA TTATTGTTGG
4621  AAGAGGACTA TTTGCAAAGG GAAGGGATGC TAAGGTAGAG GGTGAACGTT ACAGAAAAGC
4681  AGGCTGGGAA GCATATTTGA GAAGATGCGG CCAGCAAAAC TAAAAAACTG TATTATAAGT
4741  AAATGCATGT ATACTAAAAT CACAAATTAG AGCTTCAATT TAATTATATC AGTTATTACC
4801  CGGAATCTCG GTCGTAATG ATTTTTTATAA TGACGAAAAA AAAAAAATTG GAAAGAAAAA
4861  GCATGCGTCG AGTTTATCAT TATCAATACT CGCCATTTCA AAGAATACGT AAATAATTAA
4921  TAGTAGTGAT TTTCCTAACT TTATTTAGTC AAAAAATTAG CCTTTTAATT CTGCTGTAAC
4981  CCGTACATGC CAAAATAGGG GGCGGGTTAC ACAGAATATA TAACACTGAT GGTGCTTGGG
5041  TGAACAGGTT TATTCCTGGC ATCCCACTAAA TATTGTTTTC CCCGCTTTTT AAGCTGGCAT
5101  CCAGAAAAAA AAAGAATCCC AGCACCAAAA TATTGTTTTC TTCACCAACC ATCAGTTCAT
5161  AGTTCCATTC TCTTAGCGCA ACTACAGAGA ACAGGGCACA AACAGGCAAA AAACGGGCAC
5221  AACCTCAATG GAGTGATGCA ACCTGCCTGG AGTAAATGAT GACACAAGGC AATTGACCCA
5281  CGCATGTATC TATCTCATTT TCTTACACCT TCTATTACCT TCTGCTCTCT CTGATTTGGA
5341  AAAAGCTGAA AAAAAAGGTT TAAACCAGTT CCCTGAAATT ATTCCCCTAC TTGACTAATA
5401  AGTATATAAA GACGGGTAGGT ATTGATTGTA ATTCTGTAAA TCTATTTCTT AAACTTCTTA
```

→ Sequence of URA3

SphI cleavage site (boxed: GCATGC at position 4861)

← Sequence of GAP promoter

Fig. 10

```
5461  AATTCTACTT TTATAGTTAG TCTTTTTTTT AGTTTTAAAA CACCAAGAAC TTAGTTTCGA
5521  ATAAACACAC ATAAATAAAC AAAGAATTCG TCGACGGATC CCTCGAGATT GAATTGAATT
5581  GAAATCGATA GATCAATTTT TTTCTTTTCT CTTTCCCCAT CCTTTACGCT AAAATAATAG
5641  TTTATTTTAT TTTTTGAATA TTTTTTATTT ATATACGTAT ATATAGACTA TTATTTACTT
5701  TTAATAGATT ATTAAGATTT TTATTAAAAA AAAATTCGTC CCTCTTTTTA ATGCCTTTTA
5761  TGCAGTTTTT TTTTCCCATT CGATATTTCT ATGTTCGGGT TTCAGCCGTAT TTTAAGTTTA
5821  ATAACTCGAA AATTCTGCGT TTCGAAAA
```

→ PDI gene insertion site

↔ Sequence of PGK terminator

Fig. 11
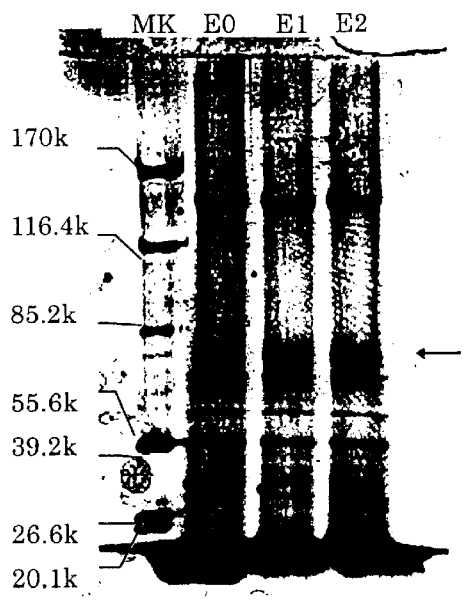
(A) Computerized image of SDS-PAGE gel of culture medium concentrate
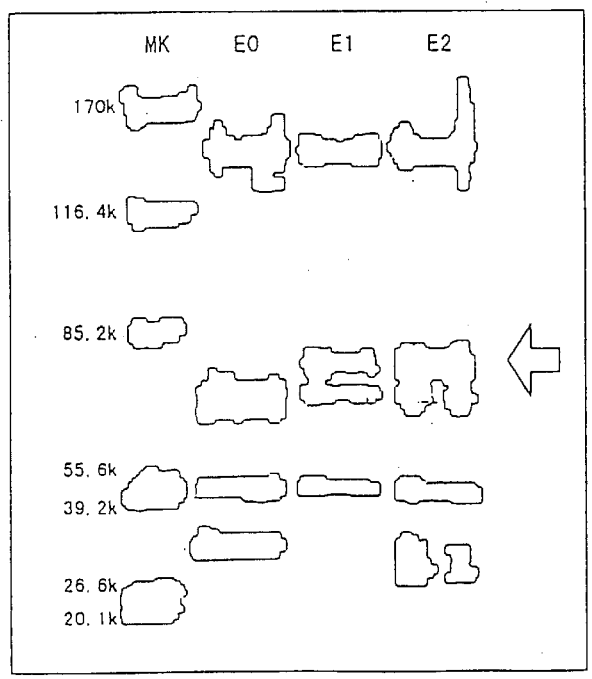
(B) Schematic representation of SDS-PAGE gel of culture medium concentrates
MK: Marker, unit of molecular weight : Da
⇐ : PDI

RECOMBINANT YEAST PDI AND PROCESS FOR PRODUCTION THEREOF

This application is a continuation of PCT/JP98/00498 filed Feb. 6, 1998.

BACKGROUND OF THE INVENTION

This invention relates to a recombinant protein of a yeast-derived enzyme, protein disulfide isomerase (hereinafter referred to as "PDI"), and a process for production thereof.

According to the present invention, a region within yeast PDI gene encoding the endoplasmic reticulum localization signal at the C-terminal is modified, the modified gene is incorporated into an expression vector, and is expressed. The recombinant yeast PDI then can be secreted outside cells, with its enzymatic activity being fully retained, and thus can be produced in a large amount. Further, the process for production according to the invention provide a yeast PDI recombinant protein under culture conditions of pH close to neutrality, by employing host cells which can be cultured at nearly neutral pH.

PDI is an enzyme (EC 5.3.4.1.), which catalyzes disulfide exchange in a protein. This enzyme promotes exchange of disulfide bonds in a protein in the presence of an appropriate oxidizing or reducing agent. The PDI protein is localized in the lumen of an endoplasmic reticulum in an eukaryote, and has the activity of catalyzing the binding of disulfide bonds of a secretory protein, which has been translated by a membrane-attached ribosome and transported to the endoplasmic reticulum. It is expected that PDI can be used to act on various proteins produced by gene recombination, and to make these proteins take stereostructures with which they can show activity. Commercially, this enzyme can be applied, for example, to improving the quality of protein-containing foods, such as dough, ham, sausages, fish paste products, and soybean curd. As noted from these facts, PDI is a useful enzyme.

Genetic engineering techniques in recent years have resulted in the disclosure of genes encoding PDI. Japanese Patent Public Disclosure No. 197176/92 describes the physicochemical properties of PDI derived from the yeast Saccharomyces cerevisiae, and a gene sequence encoding the protein. The Saccharomyces cerevisiae-derived PDI protein has a molecular weight of about 70,000 and an isoelectric point of about 4.0 to 4.1. Its optimal pH is about 8.5 to 8.75 (J. Biochem., 108, 846 (1990), Japanese Patent Public Disclosure No. 197176/92).

Usually, yeast PDI is present in cells. In order to obtain this enzyme, it was necessary to perform a complicated process comprising culturing the cells, grinding the cells, extracting and purifying cell extract and obtaining a final product. This complicated extraction process simply led to a build up of cost. Furthermore, the yeast PDI is an enzyme having the unstable property of being easily deactivated by heat or heavy metal ions. Because of this unstable property, in addition to said complexity of the extraction step, a careful, tiresome manipulation is required for maintaining the activity during the entire process.

It is one of the important challenges to produce the PDI protein, which is a useful substance, stably and in a large amount with its enzyme activity being fully retained, and supply it to the market in a fully active state. To attain this purpose, the extraction step needs to be simplified. Means for allowing the enzyme, an intracellular substance, to be secreted and produced extracellularly is effective for its simplification. Namely, if the enzyme can be continuously produced in a culture medium outside cells, which have once been cultured, the frequency of culturing the cells will be decreased, and the cell grinding step will become unnecessary. Purification from the culture medium with few impurities could simplify the purification step as well, reduce influence on the activity, and result in efficient mass production.

Yeast PDI, at the stage of a precursor, retains an extracellular secretion signal, and is produced in an endoplasmic reticulum, which is the starting point of a secretion pathway. However, even if expression is attempted so that yeast PDI will be secreted outside the cell, the wild type is not secreted extracellularly (M. Lamantia et al., Cell, 74, 899, 1993). It is speculated that this is because an endoplasmic reticulum localization signal at the C-terminal (the amino acid sequence HDEL in the case of Saccharomyces cerevisiae, for example) is retained. The number of PDI genes per cell of yeast is only one, and the amount of PDI produced per cell is minuscule. Even if the PDI is secreted in a culture medium, it cannot be obtained in sufficient concentration.

Further, the yeast PDI activity is unstable in an acidic region, while the optimum pH for ordinary yeast is in a weakly acidic region. In this weak acidity (pH 6.0 or lower), PDI is deactivated. At pH in a region in which PDI is not deactivated, yeast cells, usually, cannot remain active. In addition, culture medium components ordinary used for culture of yeast may contain substances which decrease or destroy PDI activity. The use of a culture medium containing such components would deactivate PDI produced extracellularly. For these various reasons, a method for mass production of yeast PDI in an active state had not been developed before the present invention.

SUMMARY OF THE INVENTION

The present invention provides a process suitable for mass production of recombinant yeast protein disulfide isomerase which is biologically active. Specifically, the process for production of the present invention is characterized by producing the yeast PDI protein by a genetic engineering technology using a yeast PDI gene, and causing its extracellular secretion.

The invention also provides recombinant yeast protein disulfide isomerase produced by the process for production of the present invention.

BRIEF DESCRIPTION OF THE DRAWINGS

FIGS. 2 to 4, altogether, are a series of views showing the base sequence of the PDI gene derived from Saccharomyces cerevisiae (SEQ ID NOs: 1 and 2);

FIG. 5 is a view showing a restriction map of yeast expression vector, YEp1GII;

FIGS. 6 to 10, altogether, are a series of views showing the full-length base sequence of the yeast expression vector YEp1GII (SEQ ID NO: 3); and FIG. 11(A) is a computerized image of an electrophoresis on SDS-PAGE gel of concentrated cultures of various types of transformed yeast, while FIG. 11(B) is a schematic representation of the image in FIG. 11(A).

DETAILED DESCRIPTION OF THE INVENTION

Figure 1:
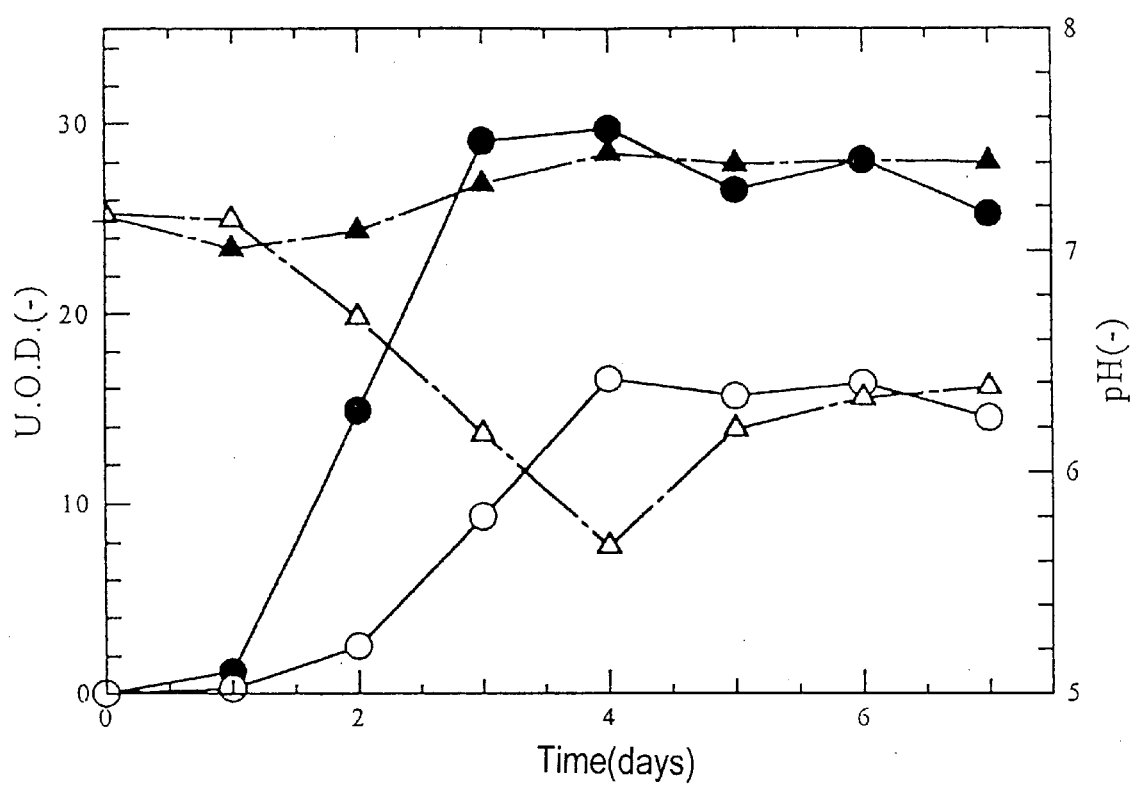
FIG. 1 is a view showing the progress of culture of Saccharomyces cerevisiae P1 and Y3 in a region close to neutral pH.

The inventors of the present invention conducted extensive studies in an attempt to solve the foregoing problems.

As a result, they prepared yeast PDI by genetic engineering, thereby making possible the mass production of this enzyme in an extracellular setting, with its enzyme activity being fully retained.

Specifically, the inventors modified yeast PDI gene, which was obtained from chromosomal DNA derived from the yeast Saccharomyces cerevisiae (H. Tachikawa et al., J. Biochem., 110, 306–313, 1991) (donated by Mr. Tachikawa), by gene recombination technology so as not to code for the C-terminal four-amino acid sequence H (histidine), D (aspartic acid), E (glutamic acid) and L (leucine), an endoplasmic reticulum localization signal. They linked this modified gene to a highly active promoter, and introduced the product into host cells, which can multiply in a culture medium at nearly neutral pH, by using a multi-copy type vector, such as YEp, to transform the cells. The transformed microorganism was cultured in a culture medium free of a yeast PDI activity inhibitor, such as a uracil-free minimal medium, with pH being kept nearly neutral using a HEPES buffer. As a result, a large amount of yeast PDI having enzyme activity was expressed in the culture medium outside the cells to complete the present invention.

In summary, the present invention is a process for producing biologically active recombinant yeast protein disulfide isomerase, comprising the steps of:

a) deleting, substituting, or adding one or more bases in a region encoding an endoplasmic reticulum localization signal of a gene encoding protein disulfide isomerase of yeast to modify the gene so as not to encode part or all of the endoplasmic reticulum localization signal;

b) incorporating said modified gene into an expression vector;

c) transforming host cells with said expression vector; and d) culturing said host cells transformed with said expression vector in a culture medium kept at nearly neutral pH, thereby causing protein disulfide isomerase to be secreted in an active state outside the host cells.

Preferably, the secreted enzyme is further concentrated or purified.

According to an aspect of the present invention, the endoplasmic reticulum localization signal is a C-terminal four-amino acid sequence (HDEL).

According to another aspect of the present invention, the expression vector is the yeast expression vector, YEp1GII, shown in FIG. 5.

According to still another aspect of the present invention, the host cells are cultured with the pH being kept at 6.5 to 8.

The present invention also provides recombinant yeast protein, a disulfide isomerase produced by the above process for production of the present invention.

The present invention also includes the expression vector and the transformed host cells used in the process for production.

Yeast PDI Gene

In the present invention, the yeast PDI gene may be, but is not restricted to, the PDI gene derived from the yeast Saccharomyces cerevisiae described, for example, as SEQ ID: No. 1 (FIGS. 2 to 4). The PDI gene derived from the yeast Saccharomyces cerevisiae is also disclosed in H. Tachikawa et al., J. Biochem., 110, 306–313, 1991, and Japanese Patent Public Disclosure No. 197176/92. PDI is considered to be present in various types of yeast in addition to Saccharomyces cerevisiae. The enzyme present in such yeast other than Saccharomyces cerevisiae, which, in a native form, has an endoplasmic reticulum localization signal, can be used in the process of the invention. For example, PDI genes derived from yeast, such as Pichia or Kluyveromyces, may also be used. PDI genes can be obtained based on the foregoing prior art references by any conventionally used techniques such as hybridization or PCR.

In eukaryotic cells, secretion of protein is performed usually along the following pathway: A secretory protein is translated from mRNA by the ribosome. After or during translation, the protein is transferred into the endoplasmic reticulum, and further transported to the Golgi apparatus, from which it is allocated to the vacuole, the cell membrane, the cell wall, or the outside of the cell. Protein, which should remain in the endoplasmic reticulum, also takes the same route as the secretory protein, but once transported to the Golgi apparatus, it is sent back to the endoplasmic reticulum. To remain in the endoplasmic reticulum, these proteins localized in the endoplasmic reticulum contain in their structure a special structure in addition to a signal necessary for entry into the secretion pathway, such as a particular amino acid sequence comprising several residues (consensus sequence), or a consensus sequence called "motif" in which amino acid residues with similar properties may be substituted conservatively. In the present specification, such a special structure necessary for persistent presence in the endoplasmic reticulum is designated as an "endoplasmic reticulum localization signal."

According to the present invention, one or more bases are deleted, substituted, or added in a region of a gene encoding an endoplasmic reticulum localization signal of PDI protein to modify the gene so as not to encode part or all of the endoplasmic reticulum localization signal.

As for Saccharomyces cerevisiae, for example, the endoplasmic reticulum localization signal consists of four amino acid residues (HDEL) at the C-terminal. Other yeasts may have an endoplasmic reticulum localization signal of a different sequence. In any case, the recombinant yeast PDI modification product such that the gene is modified so as not to encode part or all of the endoplasmic reticulum localization signal, and the expressed recombinant PDI protein is not localized in the endoplasmic reticulum, but is secreted outside the cells.

Modification of the region encoding the endoplasmic reticulum localization signal can be achieved by any of many known techniques. Mutation can be introduced at a particular position by synthesizing an oligonucleotide containing a mutant sequence adjacent to restriction sites which can be connected to a fragment of a native sequence. After connection, the resulting reconstituted sequence encodes a modified variant having desired insertion, replacement or deletion of amino acid(s) in the endoplasmic reticulum localization signal.

Alternatively, a modified gene having a particular codon modified by a necessary deletion, substitution or addition can be provided by using a site-specific mutagenic producer governed by an oligonucleotide. Techniques for performing such modification include those described in Walder et al. (Gene 42:133, 1986); Bauer et al. (Gene 37:73, 1985); Craik (BioTechniques, Jan. 12–19, 1985); Smith et al. (Genetic Engineering: Principles and Methods, Plenum Press, 1981); and U.S. Pat. Nos. 4,518,584 and 4,737,462). These documents are cited in the present specification.

The gene of the recombinant yeast PDI modified variant of the present invention is modified so as not to encode part or all of the endoplasmic reticulum localization signal, but such variant still has biologic activity. That is, this product retains its enzymatic activity of catalyzing disulfide exchange in a protein.

Furthermore, an analogue, which differs from a native amino acid sequence in terms of a region other than the endoplasmic reticulum localization signal region, but has the biological activity of PDI, is included in the recombinant yeast PDI of the present invention. The analogue, for example, can contain a conservatively substituted sequence, and one or more amino acid residues of native PDI protein can be substituted by different residues. The conservatively substituted PDI protein is shown to retain desired biological activity essentially comparable to that of the native protein. An example of a conservative substitution is the substitution for amino acids which do not change a secondary and/or a tertiary structure of PDI. A person skilled in the art can easily perform deletion, substitution or addition of one or more bases of the sequence in a portion of yeast PDI gene other than a coding region for the endoplasmic reticulum localization signal by the use of the above-described publicly known genetic engineering techniques to obtain an analogue to yeast PDI. A naturally occurring analogue to yeast PDI, e.g., allyl, is also included in the yeast PDI of the present invention. Moreover, modification can be carried out such that a yeast PDI derivative is produced by forming a covalent bond or a cohesive bond to other chemical residue, such as a glycosyl group, a lipid, a phosphate, or an acetyl group.

Expression Vector and Host Cells

The present invention provides a recombinant expression vector for expression of recombinant yeast PDI, and host cells transformed with the expression vector. Any suitable expression system can also be used. Preferred is a yeast expression system. The expression vector includes a gene encoding a yeast PDI modified variant, which has been operably linked to a suitable transcriptional or translational regulatory nucleotide sequence, such as one derived from a microbial (e.g., yeast), mammalian, viral or insect gene. Examples of the regulatory sequence include a transcription promoter, operator or enhancer, a ribosome binding site of mRNA, and appropriate sequences which control the initiation and termination of transcription and translation. To enable mass expression of the modified variant of yeast PDI, it is preferred to incorporate a powerful transcription promoter sequence into the expression vector. Generally, moreover, a replication origin which imparts replicability in the desired host cells, and one or more selectable markers for identifying transformed cells may be incorporated into the expression vector.

The expression vector of the invention is obtained in the following manner, for example: Yeast PDI gene and DNAs serving as a promoter and a vector, in accordance with the method described in Biochem. Biophys. Acta, 72, 619–629, 1963, are digested with restriction enzymes, such as EcoRI and BamHI, and then ligated by a ligase such as T4DNA ligase, as in the method described in J. Mol. Biol., 96, 171–184, 1974.

Suitable host cells suitable for the expression of the yeast PDI modified variant include yeasts, prokaryotic cells or higher eukaryotic cells. Suitable cloning and expression vectors for use together with yeasts, bacteria, fungal and mammalian cellular hosts are described, for example, in Powels et al., Cloning Vectors: A Laboratory Manual, Elsevier, N.Y. (1985)).

Yeast PDI can be expressed, preferably, in a yeast host, and more preferably, in the genus Saccharomyces (e.g., Saccharomyces cerevisiae). Other genera of yeast, such as Pichia or Kluyveromyces, may also be used. Yeast vectors will often contain an origin of replication sequence from a $2\mu$ yeast plasmid, an autonomously replicating sequence (ARS), a promoter region, sequences for polyadenylation, sequences for termination of transcription, and a selective marker.

Particular examples of the promoter sequence suitable for the yeast vector include promoters of metallothionein, 3-phosphoglycerate kinase (PGK) (Hitzeman et al., J. Biol. Chem. 255:2073, 1980), or other glycolytic enzymes (Hess et al., J. Adv. Enzyme Reg. 7:149, 1968; and Holland et al., Biochem. 17:4900, 1978), such as enolase, glyceraldehyde-3-phosphate dehydrogenase, hexokinase, pyruvate decarboxylase, phosphofructokinase, glucose-6-phophate isomerase, 3-phosphoglycerate mutase, pyruvate kinase, triosephosphate isomerase, phosphoglucose isomerase, and glucokinase. Other suitable vectors and promoters for use in yeast expression are further described in Hitzeman, EPA-73, No. 657. Glucose-repressible ADH1 (Bennetzen et al., J. Biol. Chem. 257:3018, 1982) or ADH2 (Russell et al., J. Biol. Chem. 258:2674, 1982; and Beier et al., Nature 300:724, 1982) may also be used. GAL1 and GAL10 (St. John et al., Cell 16:443, 1979; and St. John et al., J. Mol. Biol. 152:285, 1981) are also usable. A shuttle vector capable of replicating in yeast or *Escherichia coli* can be constructed by inserting a DNA sequence (Amp-resistant gene and replication origin) from pBR322 (ATCC37017) for selection and replication in *E. coli* into the foregoing yeast vector.

The preferred expression vector in yeast host cells is yeast-derived YEpGII (Japanese Patent Public Disclosure No. 289267/95) shown, for example, in FIGS. 5 to 10.

Instead of yeast host cells, it is possible to use a prokaryote, such as gram negative or gram positive organisms (e.g., *E. coli* or Bacilli), as host cells. Examples of the prokaryotic host cells suitable for transformation include *E. coli, Bacillus subtilis, Salmonella typhimurium*, and various other species of the genera Pseudomonas, Streptomyces and Staphylococcus.

The expression vector for use in the prokaryotic host cells generally includes one or more phenotypic selectable marker genes. A phenotypic selectable marker gene is, for instance, a gene encoding a protein which confers antibiotic resistance or that supplies an autotrophic requirement. Examples of the expression vector useful for prokaryotic host cells include those from commercially available plasmids, such as cloning vector pBR322 (ATCC37017). Other commercially available vectors include, for example, pKK223-3 (Pharmacia Fine Chemicals, Uppsala, Sweden) and pGEM1 (Promega Biotec, Madison, Wis., U.S.A.).

The promoter sequence commonly used for the recombinant prokaryotic host cell expression vector includes, for example, β-lactamase (penicillinase), lactose promoter system (Chang et al., Nature 275:615, 1978; and Goeddel et al., Nature 281:544, 1979), tryptophan (trp) promoter system (Goeddel et al., Nucl. Acids Res. 8:4057, 1980; and EPA-36776), T7 promoter system (Davanloo et al., Proc. Natl. Acad. Sci. USA 81:2035, 1984), and tac promoter (Maniatis, Molecular Cloning:A Laboratory Manual, Cold Spring Harbor Laboratory, 412, 1982). Phage $\lambda P_L$ promoter, and cI857ts heat-labile repressor sequence can also be used.

Alternatively, a mammalian or insect host cell culture system is also usable for expression of the recombinant yeast PDI modified variant. The expression vector for use in the mammalian host cells can be constructed as disclosed, for example, by Okayama and Berg (Mol. Cell Biol. 3:280, 1983).

As stated above, host cells selected from wide ranges can be used in the present invention. However, yeast PDI is deactivated under weakly acidic (pH 6.0) conditions. Thus, it is desirable to select and use host cells which can be proliferated and cultured under nearly neutral pH conditions. A person skilled in the art can select suitable host cells on the basis of the descriptions in the present specification. The preferred host cells can also be obtained by publicly known genetic engineering technologies or mating techniques. Alternatively, the preferred host cells can be selected from naturally occurring mutants.

For instance, the optimal pH for multiplication of yeast is, usually, in a weakly acidic region. However, yeast, which can grow in a culture medium at pH close to neutrality can be screened, for example, by the method described in Example 1. Preferably, Saccharomyces cerevisiae P1 (Oriental Yeast Co., Ltd.) can be used as host cells in the process for production of the present invention. Alternatively, instead of yeast cells, there can be selected and used a prokaryotic, mammalian or insect cell culture system which can be allowed to proliferate and culture under nearly neutral pH conditions.

Expression of Yeast PDI Variant

The selected desirable host cells can be transformed with the expression vector by the use of a publicly known technique. For example, a transformation protocol for yeast is described in Hinnen et al., Proc. Natl. Acad. Sci. USA 75:1929, 1978.

The transformed host cells are cultured under conditions which are adapted for expression of a recombinant yeast PDI modified variant, depending on the type of the host cell. Culture is performed under nearly neutral pH conditions, preferably, at pH 6.5 to 8.0. The recombinant yeast PDI modified protein expressed by the process of the present invention is secreted outside the host cells. In order for the secreted PDI protein to be maintained stably, a buffer such as HEPES is used on the culture medium for the transformants, to keep the pH nearly neutral. To exclude a substance inhibitory to yeast PDI protein activity, it is preferred to use a minimal medium as the culture medium, or add a chelating agent. As the culture medium, it is possible to use, but without restriction to, a uracil-free minimal medium (6.7 g/L yeast nitrogen base without amino acid (Difco), 20 g/L glucose, 20 mg/L adenine, 10 mg/L L-histidine, 60 mg/L L-leucine, 20 mg/L L-tryptophan, 100 mM HEPES, 10 mM EDTA-2Na, pH 7.5).

The yeast PDI modified protein produced by the process of the present invention can be purified by a publicly known method. In this invention, the recombinant protein is secreted out of the cells. Thus, the cultured broth can be concentrated using a commercially available protein concentration filter, e.g., Amicon or Millipore Pellicon ultrafiltration device. Following the concentration step, the concentrate can be applied to a purification matrix such as a gel filtration medium. Alternatively, an anion exchange resin, e.g., a matrix or substrate having pendant diethylaminoethyl (DEAE) groups, can be used. The matrices can be acrylamide, agarose, dextran, cellulose, or other types commonly employed in protein purification. A cation exchange step may also be used. As suitable cation exchangers, various insoluble matrices comprising sulfopropyl groups or carboxymethyl groups are available. Finally, to further purify the PDI protein, one or more reverse phase high performance liquid chromatography (RP-HPLC) steps employing hydrophobic RP-HPLC base media (e.g., silica gel having pendant methyl or other aliphatic groups) can be employed. Some or all of the foregoing purification steps are used in various combinations to provide a purified yeast PDI modified protein.

The secreted recombinant protein from a yeast host cell fermentation can be purified, for example, by the same method as disclosed by Urdal et al. (J. Chromatog. 296:171, 1984).

The yeast PDI modified protein is purified, for example, such that protein bands corresponding to other proteins are not detectable by SDS-polyacrylamide gel electrophoresis (SDS-PAGE). Protein bands can be visualized by silver staining, Coomassie blue staining, or autoradiography (when the protein is radiolabeled).

PDI Enzyme Activity

The recombinant yeast PDI modified protein of the present invention has a modified endoplasmic reticulum localization signal portion, but still retains PDI biological activity. The enzymatic activity of the PDI protein can be measured by a publicly known technique. The in vitro activity can be measured by the restoration of activity or the like using a reductively denatured enzyme as a substrate. For example, the measurement can be made by using, but not restricted to, the method described in Example 5 that is a modification of the method of Mizunaga et al. (J. Biochem., 108, 846, 1990). That is, the activity of RnaseA, whose activity has been restored by the action of PDI, is measured by modifying in accordance with the method of Uchida (Course of Lectures on Biochemical Experiments 2, page 68, Tokyo Kagaku Dozin Co., Ltd., 1976).

The present invention will be described in detail by way of the following Examples, which in no way limit the technical scope of the invention. A person skilled in the art can easily modify and change the invention on the basis of descriptions in the present specification, and all such modifications and changes are included within the technical scope of the invention.

EXAMPLES

Example 1 Selection of Host Cells for Production of Yeast PDI

Host cells for production of PDI having activity even at nearly neutral pH were selected by the following method:

For preliminary culture, 5 mL of a uracil-free minimal medium shown in Table 1 was placed in a 16 mm-diameter test tube. The culture medium was separately inoculated with a loopful of each of the yeasts P1, Y3 and X3 (all products of riental Yeast), and shake cultured for a whole day at 30° C.

TABLE 1

| Composition of uracil-free minimal medium (pH 7.5) Yeast nitrogen base without amino acid | |
|---|---|
| (Difco) | 0.67% |
| Glucose | 2.0% |
| Adenine | 2.0% |
| L-histidine | 1.0% |
| L-leucine | 6.0% |
| L-tryptophan | 2.0% |

Then, full-scale culture was performed at nearly neutral pH. A Sakaguchi flask was charged with 100 mL of a YPAD medium (10 g/L yeast extract, 20 g/L peptone, 140 mg/L adenine, 20 g/L glucose) that was adjusted to pH 7.5 by the addition of 100 mM HEPES. To this medium, 1 mL of the above-mentioned preculture fermentation mash was added, and the mixture was shake cultured at 30° C. and 105 rpm.

As a result, Saccharomyces cerevisiae P1 (a product of Oriental Yeast; MATa leu2-3, 112 trpl-289 ura3-1,2 his3-532 his4-516 ade2) was selected, since it grew well and maintained above pH 7.0 for 7 days of culture.

Example 2 Modification of C-terminal Endoplasmic Reticulum Localization Signal of Yeast PDI A base sequence "CACGATGAATTG (SEQ ID NO: 10)" encoding a C-terminal endoplasmic reticulum localization signal "HDEL (SEQ ID NO: 11)" of yeast (*Saccharomyces cerevisiae*) PDI was substituted by "CACGATTAATTG (SEQ ID NO: 12)" so that a termination codon could be inserted midway in the endoplasmic reticulum localization signal.

Both ends of a 6,386 bp long fragment between EcoRI-XhoI cleavage sites containing a PDI structural gene (Tachikawa et al., J. Biochem. 110:306, 1991; kindly provided by Mr. Tachikawa) on the 3rd chromosome of a yeast laboratory strain, *Saccharomyces cerevisiae* TM5, were modified to BamHI cleavage sites. Then, the modified gene was inserted between BamHI cleavage sites of *Escherichia coli* vector pUC18 to construct pUCPDI. The portion between SalI-EcoRV cleavage sites, which contains a PDI structural gene region and a termination codon, was transfered from the resulting plasmid pUCPDI into between SalI-SmaI cleavage sites of commercially available *E. coli* vector pUC19 to construct pUCPDIC1.

Then, a termination codon (TAA) was introduced into the sequence encoding the endoplasmic reticulum localization signal by PCR site-specific mutation introduction. Primers for PCR are shown in Table 2(SEQ ID NOs: 4–9 respectively).

DraI cleavage sites of pUCPDIC, containing the PDI structural gene, was inserted into between the cleaved sites of YEp1GII to construct YEpGIIPDIC. As a control, YEpGI-IPDI was constructed similarly by cleaving YEp1GII with EcoRI, blunting its ends with a DNA polymerase, and inserting a portion between DraI-DraI cleavage sites of pUCPDI, which contained PDI structural gene, into an area between the cleaved sites of YEp1GII. The constructed yeast PDI expression vectors are shown in Table 3.

TABLE 3

Yeast transformation vectors

| Name | Vector | Promoter | Endoplasmic reticulum localization signal | Name of strain for introduction |
|---|---|---|---|---|
| YEp1GII | YEp1GII | — | — | E0 |
| YepGIIPDI | YEp1GII | Variant | Wild type | E1 |
| YepGIIPDIC | YEp1GII | Variant | Variant | E2 |

TABLE 2

Primers used in PCR

| Primer | Base sequence | Origin |
|---|---|---|
| 1 RV | 5'CAGGAAACAGCTATGAC3' | Product of TAKARA SHUZO CO., LTD. |
| 2 GPI | 5'AACGTTAGCATTTTGTTTATTTATGTGTG3' | Synthesized |
| 3 PDIN | 5'AACAAAATGAAGTTTTCTGCTGG3' | Synthesized |
| 4 M4 | 5'GTTTCCCAGTCACGAC3' | Product of TAKARA SHUZO CO., LTD. |
| 5 PDIC | 5'TAACAATTAATCGTGAATGGC3' | Synthesized |
| 6 MUT3 | 5'TGATTACGCCTAGCTTACAT3' | Product of TAKARA SHUZO CO., LTD. |

Specifically, a DNA fragment was amplified by PCR in accordance with the description of "A Guide to Genetic Engineering Products" (TAKARA SHUZO, 1995–1996) by the use of the above-mentioned plasmid pUCPDIC1 as a template, and by use of a combination of a single-strand synthetic oligonucleotide RV (TAKARA SHUZO) and PDIC (synthesized by the inventors) or a combination of MUT3 and M4 (TAKARA SHUZO). Furthermore, two types of the resulting primary amplification products were mixed, and annealed for use as a template. Then, secondary PCR was performed using a combination of RV and M4 as primers. The resulting secondary amplification product containing two types of DNA fragments was treated with SphI and EcoRI. The resulting SphI-EcoRI fragment was inserted between SphI-EcoRI cleavage sites to construct pUCPDIC2.

Furthermore, SphI-SalI restriction fragment derived from pUCPDIC2 was inserted into between SphI-SalI cleavage sites containing a promoter region and a structural gene for PDI of pUCPDI to construct pUCPDIC.

Example 3 Preparation of Expression Vector for Expression of Recombinant Yeast PDI As a multi-copy type vector for expression in yeast, YEp1GII having a base sequence shown in FIGS. 5 to 10 (Japanese Patent Public Disclosure No. 289267/95) was utilized. YEp1GII contains a GAP (glyceraldehyde 3-phosphate dehydrogenase) promoter having high promoter activity.

YEp1GII was cleaved with EcoRI, and its ends were blunted with a DNA polymerase. A portion between DraI- Example 4 Transformation of Host Cells with Expression Vector Using the yeast PDI expression vector obtained in Example 3, host cells for production of PDI, i.e., Saccharomyces cerevisiae P1, were transformed by the competent cell technique involving lithium acetate in accordance with the customary method. The strains incorporating YEp1GII was designated as E0, the yeast strain incorporating YEpGI-IPDI as E1, and the yeast strain incorporating YEpGIIPDIC as E2. The resulting transformant E2 was deposited at the National Institute of Bioscience and Human Technology, Japan (Higashi 1-1-3, Tsukuba City, Ibaragi 305, Japan) with the accession number FERM P-15951 on Nov. 15, 1996. FERM P-15951 was transferred to deposition under the Budapest Treaty on Jan. 28, 1998, and given the accession number FERM BP-6240.

Example 5 Measurement of PDI Activity

Measurement of PDI activity was made by a modification of the method of Mizunaga et al. (J. Biochem., 108, 846, 1990). That is, the activity of RnaseA, whose activity was restored by the of PDI, was measured by modifying in accordance with the method of Uchida (Course of Lectures on Biochemical Experiments 2, page 68, Tokyo Kagaku Dozin Co., Ltd., 1976).

40 $\mu$L of a sample for PDI activity measurement (or ultrapure water), 40 $\mu$L of 2.5×PE buffer (125 mM $NaH_2PO_4$, 6.25 mM EDTA-2Na, pH 7.5), and 10 $\mu$L of 0.1 mM dithiothreitol (within 2 hours after preparation) were mixed in a 1.5 mL Eppendorf tube. Then, the mixture was preincubated for 5 minutes at 30° C. To the preincubated mixture, 10 μL of a solution of 5 mg/mL RNaseA and scrambled disulfide bonds (SIGMA) prepared with 10 mM acetic acid (or 10 μL of 10 mM acetic acid only) was added, where PDI reaction was then performed for 10 to 30 minutes at 30° C. Separately, 1 mL of 2 mg/mL RNA (TypeXI, SIGMA) prepared using autoclaved TKM buffer (50 mM tris, 5 mM magnesium chloride, 25 mM potassium chloride, pH 7.5) was placed in a 1.5 mL Eppendorf tube, and preincubated for 8 minutes at 37° C. To the preincubated liquid, 10 μL of the above-mentioned PDI reaction mixture was added, and the resulting mixture was subjected to RNaseA reaction for 3 minutes at 37° C. Then, 150 μL of the RNaseA reaction mixture was taken, and mixed with 50 μL of a modified uranyl reagent (a reagent formed by dissolving 0.75% uranyl acetate in 10% perchloric acid) that had been placed in another Eppendorf tube. The resulting mixture was centrifuged for 5 minutes at 12,000 rpm. Then, 40 μL of the supernatant was taken out into a cuvette, diluted with 1 mL ultra-pure water heated to 37° C., and measured at 37° C. for absorbance at 260 nm.

"One unit (1U) of PDI" was defined as enzymatic activity which restored 1U RNaseA over 1 minute at pH 7.5 and 30° C. "One unit (1U) of RNaseA" was defined as enzymatic activity which increased absorbance by 1 over 1 minute, when the absorbance was measured with a spectrophotometer at 260 nm in the foregoing method (in which the RNaseA reaction mixture was diluted 1:200/150×1040/40 on termination of the reaction and dilition).

Example 6 Selection of Culture Medium not Inhibiting PDI Activity

A yeast culture medium for production of yeast PDI was selected by mixing a crude enzyme solution, which was extracted from yeast cells, with a culture medium, and measuring the PDI activity.

A loopful of yeast (Saccharomyces cerevisiae) was inoculated into a 16 mm-diameter test tube containing 5 mL of a uracil-free minimal medium (6.7 g/L yeast nitrogen base without amino acid (Difco), 20 g/L glucose, 20 mg/L adenine, 10 mg/L L-histidine, 60 mg/L L-leucine, 20 mg/L L-tryptophan, 100 mM HEPES, 10 mM EDTA-2Na, pH 7.5). The inoculum was shake cultured for 3 days at 30° C. to prepare a crude enzyme solution from the cells. The cultured broth was centrifuged for 5 minutes at 3,000 rpm. The centrifuged cells were washed twice with ice cooled 4×PE buffer (200 mM NaH$_2$PO$_4$, 10 mM EDTA-2Na, pH 7.5) to obtain the cells. To these cells, 300 μL of 4×PE buffer was added to make a cell suspension (total volume of about 600 μL). The cell suspension (about 300 μL) was added into a 1.5 mL Eppendorf tube containing about 0.4 g of glass beads (average diameter: 0.40–0.45 mm). The Eppendorf tube was shaken for 10 minutes at a maximum speed by means of a micro tube mixer (MT-360, Tomy Seiko) in a refrigerator to grind the cells. Upon completion of grinding, the Eppendorf tube was centrifuged for 15 minutes at 13,000 rpm. The supernatant was collected into another tube, and obtained as a crude enzyme solution.

Then, 20 μL of the resulting crude enzyme solution and 20 μL of a desirable culture medium were mixed to form a sample for determination of PDI activity. The PDI activity was measured by the foregoing method. The culture medium contained a buffer and a chelating agent. As the culture medium, the foregoing uracil-free minimal medium and YAD medium (10 g/L yeast extract, 20 g/L glucose, 20 mg/L adenine, 100 mM HEPES, 10 mM EDTA-2Na, pH 7.5) were each used. The results of their comparison are shown in Table 4.

TABLE 4

Selection of culture medium not inhibiting PDI activity

| Culture medium | PDI relative activity (%) |
|---|---|
| Water | 100 |
| YAD | 68 |
| Uracil-free minimal medium | 100 |

Based on Table 4, the uracil-free minimal medium was selected as a culture medium which does not inhibit PDI activity.

Example 7 Culture of Transformed Host Cells

A loopful of the transformed yeast host cells obtained in Example 4 was inoculated into a 16 mm-diameter test tube containing 5 mL of YPAD medium. The inoculum was shake cultured for 3 days at 30° C. The cultured broth was centrifuged for 5 minutes at 3,000 rpm, and then washed twice with ice cooled 4×PE buffer (200 mM NaH$_2$PO$_4$, 10 mM EDTA-2Na, pH 7.5). To cells collected after re-centrifugation, was added 2 mL of a PDI production culture medium of the above-described composition that was prepared by adding a buffer and a chelating agent to the uracil-free minimal medium. The resulting mixture was shake cultured for 15 hours at 30° C. Thereafter, the cultured broth was ice cooled, and then centrifuged for 5 minutes at 3,000 rpm to separate cells and the culture medium.

Example 8 PDI Activity of Recombinant Yeast PDI Protein

To the culture medium obtained by culture for yeast PDI production, bovine serum albumin (BSA) (a product of Wako) was added so as to make the final concentration of 0.1 g/L. Then, the mixture was placed in a centrifugal filtration tube (Millipore, Ultrafree C3LGC, fractionated molecular weight 10,000), and concentrated at 6,000 rpm and 5° C. to a total volume of about 100 μL, thereby obtaining solution containing the yeast PDI. PDI protein was secreted and expressed in the culture medium by using each of the various transformed yeasts shown in Table 3, and the PDI activity was measured by the method of Example 5. The results are shown in Table 5. The PDI activity was the highest for E2 strain (incorporating yeast PDI gene modified to a secretor type), demonstrating the effectiveness of the present invention.

TABLE 5

PDI activity of E0, E1 and E2 strains

| Experiment | Strain | Sample | PDI activity (U/mL)[*] |
|---|---|---|---|
| 1 | E0 | Culture medium | 0 |
|  | E1 | Culture medium | $0.95 \times 10^{-1}$ |
|  | E2 | Culture medium | $1.43 \times 10^{-1}$ |
| 2 | E0 | Culture medium | 0 |
|  | E1 | Culture medium | $1.15 \times 10^{-1}$ |
|  | E2 | Culture medium | $2.27 \times 10^{-1}$ |

TABLE 5-continued

PDI activity of E0, E1 and E2 strains

| Experiment | Strain | Sample | PDI activity (U/mL)[*] |
|---|---|---|---|
| 3 | E0 | Culture medium | 0 |
|  | E1 | Culture medium | $0.36 \times 10^{-1}$ |
|  | E2 | Culture medium | $0.90 \times 10^{-1}$ |

[*]PDI activity of the culture medium was expressed as that per ml of the concentrate.

Example 9 SDS-PAGE of Culture Medium

Detection of yeast PDI in the culture medium was also performed by SDS-PAGE.

The culture medium was concentrated about 60-fold by the same method as described above without the addition of BSA. The device used was ATTO's tandem minislab gel electrophoresis device (AE6450), and the method followed the Laemmli method in accordance with the attached manual. The separation gel concentration was 7.5%. For staining, BLUPRINT Fast-PAGE Stain (a product of GIBCOBRL) was used.

FIG. 11 shows a computerized image of the stained SDS-PAGE gel. Bands characteristic of the PDI-incorporating strains (E1, E2) appear around molecular weights of 70,000 daltons. A yeast PDI molecule has about 70 kDa, and the bands suggest yeast PDI. The color density of the band was higher in E2 than in E1, thus confirming the effectiveness of the present invention by SDS-PAGE as well.

Effects of the Invention

According to the process of the present invention, yeast PDI protein can be secreted in a large amount in an active state into a culture medium, and can be collected by a simple purification method.

What is claimed is:

1. A process for producing enzymatically active recombinant yeast protein disulfied isomerase, comprising the steps of:

a) deleting or substituting one or more bases in a region encoding an endoplasmic reticulum retention signal of a gene encoding protein disulfide isomerase of yeast to modify the gene so that the endoplasmic reticulum retention signal HDEL is modified to HD;

b) incorporating said gene into an expression vector;

c) transforming yeast host cells with said expression vector, wherein said yeast host cells can be proliferated and cultured under nearly neutral pH conditions; and d) culturing said host cells transformed with said expression vector in a culture medium kept at a nearly neutral pH, thereby causing protein disulfied isomerase to be secreted in an active state outside the host cells.

2. The process of claim 1, wherein the expression vector is a yeast expression vector, YEp1GII.

3. The process of claim 1, wherein the host cells are cultured with the pH being kept at 6.5 to 8.

4. The process of claims 1, further comprising the step of concentrating or purifying the protein disulfide isomerase secreted in the culture medium, subsequently to the step d).

5. The process of claim 1, wherein the yeast host cells are *Saccharomyces cerevisiae* P1.

* * * * *

SEQUENCE LISTING

<160> NUMBER OF SEQ ID NOS: 12

<210> SEQ ID NO 1
<211> LENGTH: 1569
<212> TYPE: DNA
<213> ORGANISM: Saccharomyces cervisiae
<220> FEATURE:
<221> NAME/KEY: CDS
<222> LOCATION: (1)..(1566)

<400> SEQUENCE: 1

```
atg aag ttt tct gct ggt gcc gtc ctg tca tgg tcc tcc ctg ctg ctc      48
Met Lys Phe Ser Ala Gly Ala Val Leu Ser Trp Ser Ser Leu Leu Leu
 1               5                  10                  15 gcc tcc tct gtt ttc gcc caa caa gag gct gtg gcc cct gaa gac tcc      96
Ala Ser Ser Val Phe Ala Gln Gln Glu Ala Val Ala Pro Glu Asp Ser
             20                  25                  30 ctg tcg tta agt tgg cca ccg act ctt tca atg aat aca ttc agt cgc     144
Leu Ser Leu Ser Trp Pro Pro Thr Leu Ser Met Asn Thr Phe Ser Arg
         35                  40                  45 acg act tgg tgg ctt gcg gag ttt ttt gct cca tgg tgt ggc cac tgt     192
Thr Thr Trp Trp Leu Ala Glu Phe Phe Ala Pro Trp Cys Gly His Cys
     50                  55                  60 aag aac atg gct cct gaa tac gtt aaa gcc gcc gag act tta gtt gag     240
Lys Asn Met Ala Pro Glu Tyr Val Lys Ala Ala Glu Thr Leu Val Glu
 65                  70                  75                  80 aaa aac att acc ttg gcc cag atc gac tgt act gaa aac cag gat ctg     288
Lys Asn Ile Thr Leu Ala Gln Ile Asp Cys Thr Glu Asn Gln Asp Leu
                 85                  90                  95 tgt atg gaa cac aac att cca ggg ttc cca agc ttg aag att ttc aaa     336
Cys Met Glu His Asn Ile Pro Gly Phe Pro Ser Leu Lys Ile Phe Lys
            100                 105                 110 aac agc gat gtt aac aac tcg atc gat tac gag gga cct aga act gcc     384
Asn Ser Asp Val Asn Asn Ser Ile Asp Tyr Glu Gly Pro Arg Thr Ala
        115                 120                 125 gag gcc att gtc caa ttc atg atc aag caa agc caa ccg gct gtc gcc     432
Glu Ala Ile Val Gln Phe Met Ile Lys Gln Ser Gln Pro Ala Val Ala
    130                 135                 140 gtt gtt gct gat cta cca gct tac ctt gct aac gag act ttt gtc act     480
```

-continued

```
Val Val Ala Asp Leu Pro Ala Tyr Leu Ala Asn Glu Thr Phe Val Thr
145                 150                 155                 160 cca gtt atc gtc caa tcc ggt aag att gac gcc gac ttc aac gcc acc      528
Pro Val Ile Val Gln Ser Gly Lys Ile Asp Ala Asp Phe Asn Ala Thr
                165                 170                 175 ttt tac tcc atg gcc aac aaa cac ttc aac gac tac gac ttt gtc tcc      576
Phe Tyr Ser Met Ala Asn Lys His Phe Asn Asp Tyr Asp Phe Val Ser
            180                 185                 190 gct gaa aac gca gag gat gat ttc aag ctt tct att tac ttg ccc tcc      624
Ala Glu Asn Ala Glu Asp Asp Phe Lys Leu Ser Ile Tyr Leu Pro Ser
        195                 200                 205 gcc atg gac gag cct gta gta tac aac ggt aag aaa gcc gat atc gct      672
Ala Met Asp Glu Pro Val Val Tyr Asn Gly Lys Lys Ala Asp Ile Ala
    210                 215                 220 gac gct gat gtt ttt gaa aaa tgg ttg caa gtg gaa gcc ttg ccc tac      720
Asp Ala Asp Val Phe Glu Lys Trp Leu Gln Val Glu Ala Leu Pro Tyr
225                 230                 235                 240 ttt ggt gaa atc gac ggt tcc gtt ttc gcc caa tac gtc gaa agc ggt      768
Phe Gly Glu Ile Asp Gly Ser Val Phe Ala Gln Tyr Val Glu Ser Gly
                245                 250                 255 ttg cct ttg ggt tac ttg ttc tac aat gac gag gaa gaa ttg gaa gaa      816
Leu Pro Leu Gly Tyr Leu Phe Tyr Asn Asp Glu Glu Glu Leu Glu Glu
            260                 265                 270 tac aag cct ctc ttt acc gag ttg gcc aaa aag aac aga ggt cta atg      864
Tyr Lys Pro Leu Phe Thr Glu Leu Ala Lys Lys Asn Arg Gly Leu Met
        275                 280                 285 aac ttt gtt agc atc gat gcc aga aaa ttc ggc aga cac gcc ggc aac      912
Asn Phe Val Ser Ile Asp Ala Arg Lys Phe Gly Arg His Ala Gly Asn
    290                 295                 300 ttg aac atg aag gaa caa ttc cct cta ttt gcc atc cac gac atg act      960
Leu Asn Met Lys Glu Gln Phe Pro Leu Phe Ala Ile His Asp Met Thr
305                 310                 315                 320 gaa gac ttg aag tac ggt ttg cct caa ctc tct gaa gag gcg ttt gac     1008
Glu Asp Leu Lys Tyr Gly Leu Pro Gln Leu Ser Glu Glu Ala Phe Asp
                325                 330                 335 gaa ttg agc gac aag atc gtg ttg gag tcc aag gct att gaa cct ttg     1056
Glu Leu Ser Asp Lys Ile Val Leu Glu Ser Lys Ala Ile Glu Pro Leu
            340                 345                 350 gtt aag gac ttc ttg aaa ggt gat gcc tcc cca atc gtg aag tcc caa     1104
Val Lys Asp Phe Leu Lys Gly Asp Ala Ser Pro Ile Val Lys Ser Gln
        355                 360                 365 gag atc ttc gag aac caa gat tcc tct gtc ttc caa ttg gtc ggt aag     1152
Glu Ile Phe Glu Asn Gln Asp Ser Ser Val Phe Gln Leu Val Gly Lys
    370                 375                 380 aac cat gac gaa atc gtc aac gac cca aag aag gac gtt ctt gtt ttg     1200
Asn His Asp Glu Ile Val Asn Asp Pro Lys Lys Asp Val Leu Val Leu
385                 390                 395                 400 tac tat gcc cca tgg tgt ggt cac tgt aag aga ttg gcc cca act tac     1248
Tyr Tyr Ala Pro Trp Cys Gly His Cys Lys Arg Leu Ala Pro Thr Tyr
                405                 410                 415 caa gaa cta gct gat acc tac gcc aac gcc aca tcc gac gtt ttg att     1296
Gln Glu Leu Ala Asp Thr Tyr Ala Asn Ala Thr Ser Asp Val Leu Ile
            420                 425                 430 gct aaa cta gac cac act gaa aac gat gtc aga ggc gtc gta att gaa     1344
Ala Lys Leu Asp His Thr Glu Asn Asp Val Arg Gly Val Val Ile Glu
        435                 440                 445 ggt tac cca aca atc gtc ttc tac cca ggt ggt aag aag tcc gaa tct     1392
Gly Tyr Pro Thr Ile Val Phe Tyr Pro Gly Gly Lys Lys Ser Glu Ser
    450                 455                 460
```

```
gtt gtg tac caa ggt tca aga tcc ttg gac tct tta ttc gac ttc atc    1440
Val Val Tyr Gln Gly Ser Arg Ser Leu Asp Ser Leu Phe Asp Phe Ile
465             470                 475                 480 aag gaa aac ggt cac ttc gac gtc gac ggt aag gcc ttg tac gaa gaa    1488
Lys Glu Asn Gly His Phe Asp Val Asp Gly Lys Ala Leu Tyr Glu Glu
                485                 490                 495 gcc cag gaa aag gct gct gag gaa gcc gat gct gac gct gaa ttg gct    1536
Ala Gln Glu Lys Ala Ala Glu Glu Ala Asp Ala Asp Ala Glu Leu Ala
            500                 505                 510 gac gaa gaa gat gcc att cac gat gaa ttg taa                        1569
Asp Glu Glu Asp Ala Ile His Asp Glu Leu
            515                 520

<210> SEQ ID NO 2
<211> LENGTH: 522
<212> TYPE: PRT
<213> ORGANISM: Saccharomyces cervisiae

<400> SEQUENCE: 2

Met Lys Phe Ser Ala Gly Ala Val Leu Ser Trp Ser Ser Leu Leu Leu
 1               5                  10                  15

Ala Ser Ser Val Phe Ala Gln Gln Glu Ala Val Ala Pro Glu Asp Ser
                20                  25                  30

Leu Ser Leu Ser Trp Pro Pro Thr Leu Ser Met Asn Thr Phe Ser Arg
            35                  40                  45

Thr Thr Trp Trp Leu Ala Glu Phe Phe Ala Pro Trp Cys Gly His Cys
        50                  55                  60

Lys Asn Met Ala Pro Glu Tyr Val Lys Ala Ala Glu Thr Leu Val Glu
65                  70                  75                  80

Lys Asn Ile Thr Leu Ala Gln Ile Asp Cys Thr Glu Asn Gln Asp Leu
                85                  90                  95

Cys Met Glu His Asn Ile Pro Gly Phe Pro Ser Leu Lys Ile Phe Lys
                100                 105                 110

Asn Ser Asp Val Asn Asn Ser Ile Asp Tyr Glu Gly Pro Arg Thr Ala
            115                 120                 125

Glu Ala Ile Val Gln Phe Met Ile Lys Gln Ser Gln Pro Ala Val Ala
130                 135                 140

Val Val Ala Asp Leu Pro Ala Tyr Leu Ala Asn Glu Thr Phe Val Thr
145                 150                 155                 160

Pro Val Ile Val Gln Ser Gly Lys Ile Asp Ala Asp Phe Asn Ala Thr
                165                 170                 175

Phe Tyr Ser Met Ala Asn Lys His Phe Asn Asp Tyr Asp Phe Val Ser
            180                 185                 190

Ala Glu Asn Ala Glu Asp Asp Phe Lys Leu Ser Ile Tyr Leu Pro Ser
        195                 200                 205

Ala Met Asp Glu Pro Val Val Tyr Asn Gly Lys Lys Ala Asp Ile Ala
210                 215                 220

Asp Ala Asp Val Phe Glu Lys Trp Leu Gln Val Glu Ala Leu Pro Tyr
225                 230                 235                 240

Phe Gly Glu Ile Asp Gly Ser Val Phe Ala Gln Tyr Val Glu Ser Gly
                245                 250                 255

Leu Pro Leu Gly Tyr Leu Phe Tyr Asn Asp Glu Glu Leu Glu Glu
            260                 265                 270

Tyr Lys Pro Leu Phe Thr Glu Leu Ala Lys Lys Asn Arg Gly Leu Met
        275                 280                 285

Asn Phe Val Ser Ile Asp Ala Arg Lys Phe Gly Arg His Ala Gly Asn
```

|   |   |   |   |   |   |   |   |   |   |
|---|---|---|---|---|---|---|---|---|---|
|   |   | 290 |   |   | 295 |   |   | 300 |   |
| Leu | Asn | Met | Lys | Glu | Gln | Phe | Pro | Leu | Phe |
| 305 |   |   |   | 310 |   |   |   | 315 |   |
| Ala | Ile | His | Asp | Met | Thr |   |   |   |   |
|   |   |   |   | 320 |   |   |   |   |   |

Leu Asn Met Lys Glu Gln Phe Pro Leu Phe Ala Ile His Asp Met Thr
305                 310                 315                 320

Glu Asp Leu Lys Tyr Gly Leu Pro Gln Leu Ser Glu Glu Ala Phe Asp
                325                 330                 335

Glu Leu Ser Asp Lys Ile Val Leu Glu Ser Lys Ala Ile Glu Pro Leu
            340                 345                 350

Val Lys Asp Phe Leu Lys Gly Asp Ala Ser Pro Ile Val Lys Ser Gln
        355                 360                 365

Glu Ile Phe Glu Asn Gln Asp Ser Ser Val Phe Gln Leu Val Gly Lys
    370                 375                 380

Asn His Asp Glu Ile Val Asn Asp Pro Lys Lys Asp Val Leu Val Leu
385                 390                 395                 400

Tyr Tyr Ala Pro Trp Cys Gly His Cys Lys Arg Leu Ala Pro Thr Tyr
                405                 410                 415

Gln Glu Leu Ala Asp Thr Tyr Ala Asn Ala Thr Ser Asp Val Leu Ile
            420                 425                 430

Ala Lys Leu Asp His Thr Glu Asn Asp Val Arg Gly Val Val Ile Glu
        435                 440                 445

Gly Tyr Pro Thr Ile Val Phe Tyr Pro Gly Lys Lys Ser Glu Ser
    450                 455                 460

Val Val Tyr Gln Gly Ser Arg Ser Leu Asp Ser Leu Phe Asp Phe Ile
465                 470                 475                 480

Lys Glu Asn Gly His Phe Asp Val Asp Gly Lys Ala Leu Tyr Glu Glu
                485                 490                 495

Ala Gln Glu Lys Ala Ala Glu Glu Ala Asp Ala Asp Ala Glu Leu Ala
            500                 505                 510

Asp Glu Glu Asp Ala Ile His Asp Glu Leu
        515                 520

<210> SEQ ID NO 3
<211> LENGTH: 5848
<212> TYPE: DNA
<213> ORGANISM: isolate YEp1GII

<400> SEQUENCE: 3

```
agatctgggc ctcgtgatac gcctattttt ataggttaat gtcatgataa taatggtttc      60
ttagacgtca ggtggcactt ttcggggaaa tgtgcgcgga acccctattt gtttattttt     120
ctaaatacat tcaaatatgt atccgctcat gagacaataa ccctgataaa tgcttcaata     180
atattgaaaa aggaagagta tgagtattca acatttccgt gtcgccctta ttcccttttt     240
tgcggcattt tgccttcctg ttttgctca cccagaaacg ctggtgaaag taaagatgc      300
tgaagatcag ttgggtgcac gagtgggtta catcgaactg gatctcaaca gcggtaagat     360
ccttgagagt tttcgccccg aagaacgttt tccaatgatg agcacttta aagttctgct      420
atgtggcgcg gtattatccc gtattgacgc cgggcaagag caactcggtc gccgcataca     480
ctattctcag aatgacttgg ttgagtactc accagtcaca gaaaagcatc ttacggatgg     540
catgacagta agagaattat gcagtgctgc cataaccatg agtgataaca ctgcggccaa     600
cttacttctg acaacgatcg gaggaccgaa ggagctaacc gcttttttgc acaacatggg     660
ggatcatgta actcgccttg atcgttggga accggagctg aatgaagcca taccaaacga     720
cgagcgtgac accacgatgc ctgtagcaat ggcaacaacg ttgcgcaaac tattaactgg     780
cgaactactt actctagctt cccggcaaca attaatagac tggatggagg cggataaagt     840
```

```
tgcaggacca cttctgcgct cggcccttcc ggctggctgg tttattgctg ataaatctgg    900
agccggtgag cgtgggtctc gcggtatcat tgcagcactg gggccagatg gtaagccctc    960
ccgtatcgta gttatctaca cgacggggag tcaggcaact atggatgaac gaaatagaca   1020
gatcgctgag ataggtgcct cactgattaa gcattggtaa ctgtcagacc aagtttactc   1080
atatatactt tagattgatt taaaacttca tttttaattt aaaaggatct aggtgaagat   1140
ccttttttgat aatctcatga ccaaaatccc ttaacgtgag ttttcgttcc actgagcgtc   1200
agacccccgta gaaaagatca aaggatcttc ttgagatcct ttttttctgc gcgtaatctg   1260
ctgcttgcaa acaaaaaaac caccgctacc agcggtggtt tgtttgccgg atcaagagct   1320
accaactctt tttccgaagg taactggctt cagcagagcg cagataccaa atactgtcct   1380
tctagtgtag ccgtagttag gccaccactt caagaactct gtagcaccgc ctacatacct   1440
cgctctgcta atcctgttac cagtggctgc tgccagtggc gataagtcgt gtcttaccgg   1500
gttggactca agacgatagt taccggataa ggcgcagcgg tcgggctgaa cggggggttc   1560
gtgcacacag cccagcttgg agcgaacgac ctacaccgaa ctgagatacc tacagcgtga   1620
gctatgagaa agcgccacgc ttcccgaagg gagaaaggcg gacaggtatc cggtaagcgg   1680
cagggtcgga acaggagagc gcacgaggga gcttccaggg ggaaacgcct ggtatcttta   1740
tagtcctgtc gggtttcgcc acctctgact tgagcgtcga ttttttgtgat gctcgtcagg   1800
ggggcggagc ctatgaaaaa cgccagcaa cgcggccttt ttacggttcc tggccttttg   1860
ctggcctttt gctcacatgt tctttcctgc gttatcccct gattctgtgg ataaccgtat   1920
taccgccttt gagtgagctg ataccgctcg ccgcagccga acgaccgagc gcagcgagtc   1980
agtgagcgag gaagcggaag agcgcccaat acgcaaaccg cctctccccg cgcgttggcc   2040
gattcattaa tgcagctggc acgacaggtt cccgactgg aaagcgggca gtgagcgcaa   2100
cgcaattaat gtgagttagc tcactcatta ggcacccag gctttacact ttatgcttcc   2160
ggctcgtatg ttgtgtggaa ttgtgagcgg ataacaattt cacacaggaa acagctatga   2220
ccatgattac gccaagctta cattttatgt tagctggtgg actgacgcca gaaaatgttg   2280
gtgatgcgct tagattaaat ggcgttattg gtgttgatgt aagcggaggt gtggagacaa   2340
atggtgtaaa agactctaac aaaatagcaa atttcgtcaa aaatgctaag aaataggtta   2400
ttactgagta gtatttattt aagtattgtt tgtgcacttg cctgcaggcc ttttgaaaag   2460
caagcataaa agatctaaac ataaaatctg taaaataaca agatgtaaag ataatgctaa   2520
atcatttggc tttttgattg attgtacagg aaaatataca tcgcaggggg ttgacttta   2580
ccatttcacc gcaatggaat caaacttgtt gaagagaatg ttcacaggcg catacgctac   2640
aatgacccga ttcttgctag ccttttctcg gtcttgcaaa caaccgccgg cagcttagta   2700
tataaataca catgtacata cctctctccg tatcctcgta atcattttct tgtatttatc   2760
gtcttttcgc tgtaaaaact ttatcacact tatctcaaat acacttatta accgctttta   2820
ctattatctt ctacgctgac agtaatatca aacagtgaca catattaaac acagtggttt   2880
ctttgcataa acaccatcag cctcaagtcg tcaagtaaag atttcgtgtt catgcagata   2940
gataacaatc tatatgttga taattagcgt tgcctcatca atgcgagatc cgtttaaccg   3000
gacccctagtg cacttacccc acgttcggtc cactgtgtgc cgaacatgct ccttcactat   3060
tttaacatgt ggactagtct cgggatgcat ttttgtagaa caaaaaagaa gtatagattc   3120
tttgttggta aaatagcgct ctcgcgttgc atttctgttc tgtaaaaatg cagctcagat   3180
```

-continued

```
tctttgtttg aaaaattagc gctctcgcgt tgcattttg ttttacaaaa atgaagcaca      3240
gattcttcgt tggtaaaata gcgctttcgc gttgcatttc tgttctgtaa aaatgcagct      3300
cagattcttg gtttgaaaaa ttagcgctct cgcgttgcat ttttgttcta caaatgaag       3360 cacagatgct tcgttaacaa agatatgcta ttgaagtgca agatggaaac gcagaaaatg      3420
aaccggggat gcgacgtgca agattaccta tgcaatagat gcaatagttt ctccaggaac      3480
cgaaatacat acattgtctt ccgtaaagcg ctagactata tattattata caggttcaaa      3540
tatactatct gtttcaggga aaactcccag gttcggatgt tcaaaattca atgatgggta      3600
acaagtacga tcgtaaatct gtaaaacagt ttgtcggata ttaggctgta tctcctcaaa      3660
gcgtattcga atatcattga gaagctgcag actagttttt caattcaatt catcattttt      3720
tttttattct tttttttgat ttcggtttct ttgaaatttt tttgattcgg taatctccga      3780
acagaaggaa gaacgaagga aggagcacag acttagattg gtatatatac gcatatgtag      3840
tgttgaagaa acatgaaatt gcccagtatt cttaacccaa ctgcacagaa caaaaacctg      3900
caggaaacga agataaatca tgtcgaaagc tacatataag gaacgtgctg ctactcatcc      3960
tagtcctgtt gctgccaagc tatttaatat catgcacgaa aagcaaacaa acttgtgtgc      4020
ttcattggat gttcgtacca ccaaggaatt actggagtta gttgaagcat taggtcccaa      4080
aatttgttta ctaaaaacac atgtggatat cttgactgat ttttccatgg agggcacagt      4140
taagccgcta aaggcattat ccgccaagta caattttta ctcttcgaag acagaaaatt       4200
tgctgacatt ggtaatacag tcaaattgca gtactctgcg ggtgtataca aatagcaga      4260 atgggcagac attacgaatg cacacggtgt ggtgggccca ggtattgtta gcggtttgaa      4320
gcaggcggca gaagaagtaa caaaggaacc tagaggcctt ttgatgttag cagaattgtc      4380
atgcaagggc tccctatcta ctggagaata tactaagggt actgttgaca ttgcgaagag      4440
cgacaaagat tttgttatcg gctttattgc tcaaagagac atgggtggaa gagatgaagg      4500
ttacgattgg ttgattatga cacccggtgt gggtttagat acaagggag acgcattggg       4560 tcaacagtat agaaccgtgg atgatgtggt ctctacagga tctgacatta ttattgttgg      4620
aagaggacta tttgcaaagg gaagggatgc taaggtagag ggtgaacgtt acagaaaagc      4680
aggctgggaa gcatatttga gaagatgcgg ccagcaaaac taaaaaactg tattataagt      4740
aaatgcatgt atactaaact cacaaattag agcttcaatt taattatatc agttattacc      4800
cgggaatctc ggtcgtaatg attttttaaa tgacgaaaaa aaaaaaattg gaaagaaaaa      4860
gcatgcgtcg agtttatcat tatcaatact cgccatttca agaatacgt aaataattaa       4920 tagtagtgat tttcctaact ttatttagtc aaaaaattag ccttttaatt ctgctgtaac      4980
ccgtacatgc caaaataggg ggcgggttac acagaatata taacactgat ggtgcttggg      5040
tgaacaggtt tattcctggc atccactaaa tataatggag cccgcttttt aagctggcat      5100
ccagaaaaaa aaagaatccc agcaccaaaa tattgttttc ttcaccaacc atcagttcat      5160
aggtccattc tcttagcgca actacagaga acagggcaca aacaggcaaa aaacgggcac      5220
aacctcaatg gagtgatgca acctgcctgg agtaaatgat gacacaaggc aattgaccca      5280
cgcatgtatc tatctcattt tcttacacct tctattacct tctgctctct ctgatttgga      5340
aaaagctgaa aaaaaggtt taaccagtt ccctgaaatt attccctac ttgactaata         5400 agtatataaa gacggtaggt attgattgta attctgtaaa tctattttctt aaacttctta     5460 aattctactt ttatagttag tctttttttt agttttaaaa caccaagaac ttagtttcga      5520
ataaacacac ataaataaac aaagaattcg tcgacggatc cctcgagatt gaattgaatt      5580
```

```
gaaatcgata gatcaattttt tttcttttct ctttccccat cctttacgct aaaataatag    5640
tttattttat tttttgaata ttttttattt atatacgtat atatagacta ttatttactt    5700
ttaatagatt attaagattt ttattaaaaa aaaattcgtc cctcttttta atgccttta     5760 tgcagttttt ttttcccatt cgatatttct atgttcgggt ttcagcgtat tttaagttta    5820
ataactcgaa aattctgcgt ttcgaaaa                                       5848
```

<210> SEQ ID NO 4
<211> LENGTH: 17
<212> TYPE: DNA
<213> ORGANISM: Artificial Sequence
<220> FEATURE:
<223> OTHER INFORMATION: Description of Artificial Sequence: primer

<400> SEQUENCE: 4

```
caggaaacag ctatgac                                                     17
```

<210> SEQ ID NO 5
<211> LENGTH: 29
<212> TYPE: DNA
<213> ORGANISM: Artificial Sequence
<220> FEATURE:
<223> OTHER INFORMATION: Description of Artificial Sequence: primer

<400> SEQUENCE: 5

```
aacgttagca ttttgtttat ttatgtgtg                                        29
```

<210> SEQ ID NO 6
<211> LENGTH: 23
<212> TYPE: DNA
<213> ORGANISM: Artificial Sequence
<220> FEATURE:
<223> OTHER INFORMATION: Description of Artificial Sequence: primer

<400> SEQUENCE: 6

```
aacaaaatga agttttctgc tgg                                              23
```

<210> SEQ ID NO 7
<211> LENGTH: 16
<212> TYPE: DNA
<213> ORGANISM: Artificial Sequence
<220> FEATURE:
<223> OTHER INFORMATION: Description of Artificial Sequence: primer

<400> SEQUENCE: 7

```
gtttcccagt cacgac                                                      16
```

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 8

```
taacaattaa tcgtgaatgg c                                                21
```

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: primer

```
<400> SEQUENCE: 9
tgattacgcc tagcttacat                                                    20

<210> SEQ ID NO 10
<211> LENGTH: 12
<212> TYPE: DNA
<213> ORGANISM: yeast
<220> FEATURE:
<223> OTHER INFORMATION: Description of Artificial Sequence: primer

<400> SEQUENCE: 10
cacgatgaat tg                                                            12

<210> SEQ ID NO 11
<211> LENGTH: 4
<212> TYPE: PRT
<213> ORGANISM: yeast

<400> SEQUENCE: 11

His Asp Glu Leu
  1

<210> SEQ ID NO 12
<211> LENGTH: 12
<212> TYPE: DNA
<213> ORGANISM: Artificial Sequence
<220> FEATURE:
<223> OTHER INFORMATION: Description of Artificial Sequence: SYNTHETIC
      PDI SUBSTITUTION

<400> SEQUENCE: 12
cacgattaat tg                                                            12
```